United States Patent
Fleck et al.

(10) Patent No.: US 7,129,354 B2
(45) Date of Patent: Oct. 31, 2006

(54) PROCESS FOR THE PREPARATION OF STABLE ACID ADDITION SALT OF 2,3-DISUBSTITUTED PYRAZINE COMPOUNDS

(75) Inventors: Tom Fleck, deceased, late of Scotts, MI (US); by Bruce Fleck, legal representative, Scotts, MI (US); Magnus Cernerud, Stockholm (SE); Helena Lundström, Sundbyberg (SE); Claes Löfström, Stockholm (SE); Margit Pelcman, Stockholm (SE); Alexander Paptchikhine, Uppsala (SE); Emma Andersson, Järfälla (SE); Alf Nygren, Uppsala (SE)

(73) Assignee: Biovitrum AB (SE)

( * ) Notice: Subject to any disclaimer, the term of this patent is extended or adjusted under 35 U.S.C. 154(b) by 0 days.

(21) Appl. No.: 10/464,181

(22) Filed: Jun. 18, 2003

(65) Prior Publication Data

US 2004/0038981 A1 Feb. 26, 2004

Related U.S. Application Data

(60) Provisional application No. 60/416,701, filed on Oct. 7, 2002, provisional application No. 60/406,119, filed on Aug. 26, 2002, provisional application No. 60/390,656, filed on Jun. 21, 2002.

(30) Foreign Application Priority Data

| Jun. 19, 2002 | (SE) | 0201881 |
| Jun. 28, 2002 | (SE) | 0202041 |
| Aug. 26, 2002 | (SE) | 0202516 |

(51) Int. Cl.
*C07D 241/18* (2006.01)

(52) U.S. Cl. .................................. 544/357; 546/290

(58) Field of Classification Search ................ 544/357; 546/290

See application file for complete search history.

(56) References Cited

FOREIGN PATENT DOCUMENTS

| WO | WO 00/76984 A2 | 12/2000 |
| WO | WO 00/76984 A3 | 12/2000 |

*Primary Examiner*—Venkataraman Balasubramanian
(74) *Attorney, Agent, or Firm*—Fish & Richardson P.C.

(57) ABSTRACT

The present invention relates to a process for the preparation of compounds which are therapeutically active in the central nervous system.

In one aspect, the invention relates to a process for the preparation of compounds of the general formula (I):

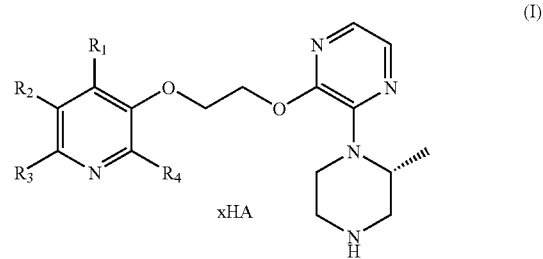

wherein HA is a pharmaceutically acceptable acid and $R_1$–$R_4$ are each independently selected from the group consisting of hydrogen, halogen, $C_1$–$C_6$-alkyl, $C_1$–$C_6$-alkoxy, and di-$C_1$–$C_6$-alkylamino-$C_2$–$C_6$-alkoxy.

The invention also relates to the use of said compound to manufacture a medicament for the treatment of a serotonin-related disorder.

11 Claims, No Drawings

PROCESS FOR THE PREPARATION OF STABLE ACID ADDITION SALT OF 2,3-DISUBSTITUTED PYRAZINE COMPOUNDS

RELATED APPLICATIONS

This application claims priority to Swedish application number 0201881-0, filed on Jun. 19, 2002, Swedish application number 0202041-0, filed on Jun. 28, 2002, Swedish application number 0202516-1, filed on Aug. 26, 2002, U.S. provisional application No. 60/390,656, filed Jun. 21, 2002, U.S. provisional application No. 60/406,119, filed on Aug. 26, 2002, and U.S. provisional application No. 60/416,701, filed on Oct. 7, 2002, the contents of which are incorporated herein by reference.

FIELD OF THE INVENTION

The present invention relates to a process for the preparation of compounds which are therapeutically active in the central nervous system.

BACKGROUND OF THE INVENTION

Many diseases of the central nervous system are influenced by the adrenergic, the dopaminergic, and the serotonergic neurotransmitter systems. For example, serotonin has been implicated in a number of diseases and conditions which originate in the central nervous system. A number of pharmacological and genetic experiments involving receptors for serotonin strongly implicate the 5-HT$_{2c}$ receptor subtype in the regulation of food intake (Obes. Res. 1995, 3, Suppl. 4, 449S–462S). The 5-HT$_{2c}$ receptor subtype is transcribed and expressed in hypothalamic structures associated with appetite regulation. It has been demonstrated that the non-specific 5-HT$_{2c}$ receptor agonist m-chlorophenylpiperazine (mCPP), which has some preference for the 5-HT$_{2c}$ receptor, causes weight loss in mice that express the normal 5-HT$_{2c}$ receptor while the compound lacks activity in mice expressing the mutated inactive form of the 5-HT$_{2c}$ receptor (Nature 1995, 374, 542–546). In a recent clinical study, a slight but sustained reduction in body weight was obtained after 2 weeks of treatment with mCPP in obese subjects (Psychopharmacology 1997, 133, 309–312). Weight reduction has also been reported from clinical studies with other "serotonergic" agents (see e.g. IDrugs 1998, 1, 456–470). For example, the 5-HT reuptake inhibitor fluoxetine and the 5-HT releasing agent/reuptake inhibitor dexfenfluramine have exhibited weight reduction in controlled studies. However, currently available drugs that increase serotonergic transmission appear to have only a moderate and, in some cases, transient effects on the body weight.

The 5-HT$_{2c}$ receptor subtype has also been suggested to be involved in CNS disorders such as depression and anxiety (Exp. Opin. Invest. Drugs 1998, 7, 1587–1599; IDrugs, 1999, 2, 109–120).

The 5-HT$_{2c}$ receptor subtype has further been suggested to be involved in urinary disorders such as urinary incontinence (IDrugs, 1999, 2, 109–120).

Compounds which have a selective effect on the 5-HT$_{2c}$ receptor may therefore have a therapeutic potential in the treatment or prophylaxis of disorders like those mentioned above. Of course, selectivity also reduces the potential for adverse effects mediated by other serotonin receptors.

Examples of such compounds are (2R)-1-(3-{2-[(2-ethoxy-3-pyridinyl)oxy]ethoxy}-2-pyrazinyl)-2-methylpiperazine, (2R)-methyl-1-{3-[2-(3-pyridinyloxy)ethoxy]-2-pyrazinyl}piperazine and pharmaceutically acceptable acid salts thereof. WO 00/76984 (hereinafter called D1) relates to a process for the preparation of such compounds on a small scale such as a gram scale. A problem to be solved by the present invention was to prepare such compounds on a large scale such as on a kilogram scale. The following factors are more important for preparation on a large scale, in comparison to preparation on a small scale:

to obtain a high yield of the desired products for economy reasons, that the processes for preparation are safe with regard to explosion, that the reagents and solvents used are relatively non-toxic, that the products obtained are relatively stable, and that the reaction times are relatively short.

These problems have been solved by the present invention. It has been shown that the yields of the desired products according to the present invention are higher than the yields according to D1. In the experimental part, the yields according to the present invention and D1 are compared. Regarding the choice of solvents for the process steps, dioxane, as used according to D1, has been replaced by solvents such as MtBE and THF (see step (ii) below) which are less prone to form peroxides and which are less carcinogenic than dioxane. Furthermore, it has been shown that (2R)-methyl-1-{3-[2-(3-pyridinyloxy)ethoxy]-2-pyrazinyl}piperazine, L-malate salt prepared according to the present invention (see Example 3A) has superior properties compared to (2R)-methyl-1-{3-[2-(3-pyridinyloxy)ethoxy]-2-pyrazinyl}piperazine, hydrochloride prepared according to D1 in that the former has a higher crystallinity, is less hygroscopic and has a higher chemical stability than the latter. Regarding chemical stability, D1 discloses the preparation of (2R)-1-(3-chloro-2-pyrazinyl)-2-methylpiperazine, which has also been prepared in Example 8 below. This compound is not stable for storage as a free base. As (2R)-1-(3-chloro-2-pyrazinyl)-2-methylpiperazine is a key intermediate, chemical stability during long term storage is important with regard to process economy. It has now been found that the corresponding hydrochloride salt thereof is considerably more stable, which has been prepared in Example 9 below.

The method to prepare Example 3C is a good way of increasing the purity of Example 2C. It has been shown that Example 2C with a purity of 60–70% gives Example 3C with a purity of 99% in one crystallization step. By contrast, the same purity increasing effect has not been achieved by making the acetate of Example 2C. Regarding reaction time, the reaction according to Example 2A below was complete at room temperature in 15 minutes. The same compound has been prepared in Example 173 in D 1. The procedure of Example 172, step 3 has been followed, wherein the reaction was stirred at 85° C. for 15 h. Furthermore, the reaction according to Example 2B below was complete in 35 minutes at 55° C. The same compound has been prepared in Example 200 in D1. The procedure of Example 192, step 3 has been followed, wherein the reaction was stirred at 90° C. for 2 h.

SUMMARY OF THE INVENTION

One object of the present invention is a process for the preparation of compounds which bind to the 5-HT$_{2c}$ receptor (agonists and antagonists) and which therefore may be used for the treatment or prophylaxis of serotonin-related disorders.

In one aspect, the invention relates to a process for the preparation of compounds of the general formula (I):

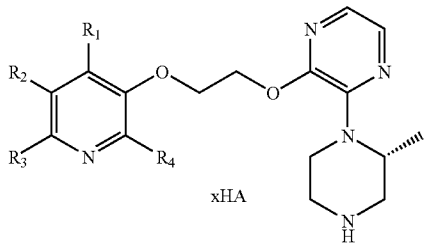

(I)

comprising the steps of:
(i) hydroxyalkylating (i.e., O-alkylating) a 3-pyridinol derivative of the general formula (II) or the corresponding hydrochloride:

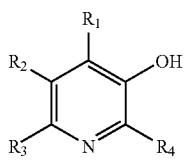

(II)

to give another 3-pyridinol derivative of the general formula (III):

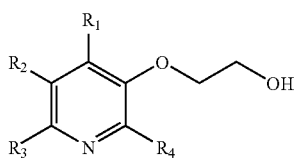

(III)

(ii) condensing the 3-pyridinol derivative of the general formula (III) with (2R)-1-(3-chloro-2-pyrazinyl)-2-methylpyrazine of the formula (IV) in the presence of an alkali metal tert-butoxide (e.g. potassium tert-butoxide) or an alkali earth metal tert-butoxide, as a base in a solvent system (e.g., a solvent system containing tetrahydrofuran),

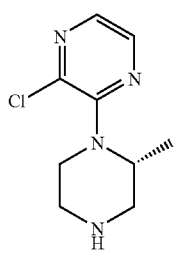

(IV)

to give a compound of the general formula (V):

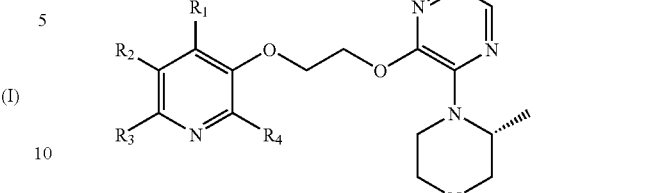

(V)

(iii) which is then converted to the compound of the general formula (I) by treatment with a pharmaceutically acceptable acid of the formula HA, wherein $R_1$–$R_4$ are each independently selected from the group consisting of hydrogen, halogen, $C_1$–$C_6$-alkyl, $C_1$–$C_6$-alkoxy, and di-$C_1$–$C_6$-alkylamino-$C_2$–$C_6$-alkoxy; and wherein (2R)-1-(3-chloro-2-pyrazinyl)-2-methylpyrazine of the formula (IV) is prepared by:

(iv) acidification of racemic 2-methylpiperazine of the formula (VI):

(VI)

with L-tartaric acid and fractional crystallization to give (R)-2-methylpiperazine, L-tartrate of the formula (VII):

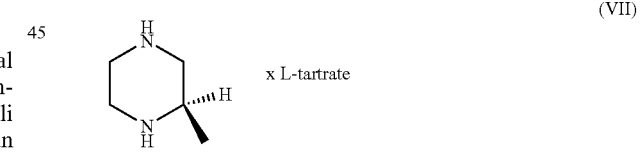

(VII)

(v) basification of (2R)-2-methylpiperazine, L-tartrate of the formula (VII) to give (R)-2-methylpiperazine of the formula (VIII):

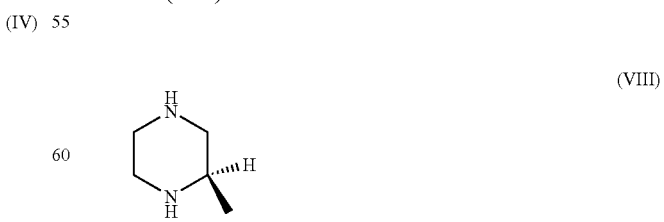

(VIII)

(vi) tritylation of (R)-2-methylpiperazine of the formula (VIII) to give (R)-3-methyl-1-tritylpiperazine of the formula (IX):

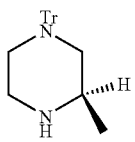

(IX)

(vii) condensation of (R)-3-methyl-1-tritylpiperazine of the formula (IX) with 2,3-dichloropyrazine to give (2R)-1-(3-chloro-2-pyrazinyl)-2-methyl-4-tritylpiperazine of the formula (X):

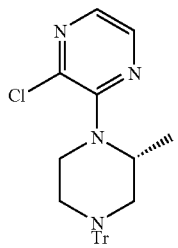

(X)

(viii) detritylation of (2R)-1-(3-chloro-2-pyrazinyl)-2-methyl-4-tritylpiperazine of the formula (X) to give (2R)-1-(3-chloro-2-pyrazinyl)-2-methylpiperazine of the formula (IV), (ix) and conversion of (2R)-1-(3-chloro-2-pyrazinyl)-2-methylpiperazine of the formula (IV) to a suitable acid addition salt (e.g, hydrochloride salt).

It is preferred that $R_1$–$R_3$ are hydrogen and $R_4$ is selected from the group consisting of hydrogen, ethoxy, and 2-dimethylaminoethoxy.

It is also preferred that:
step (iv) is performed by using water and ethanol as solvents;
step (v) is performed by using a hydroxide (e.g., sodium hydroxide) as a base;
step (vi) is performed with trityl chloride in the presence of triethylamine;
step (vii) is performed in the presence of an alkali metal carbonate (e.g. potassium carbonate) or an alkali earth metal carbonate, with dimethyl formamide as a solvent; and
step (viii) is performed in 10% sulfuric acid in isopropanol.

When $R_1$–$R_4$ are hydrogen, it is preferred that:
step (i) is performed by reacting the compound of the formula (II) with ethylene carbonate with an alkali metal carbonate (e.g. potassium carbonate) or an alkali earth metal carbonate, as a base and dimethyl formamide as a solvent,
step (ii) is performed by reacting the compound of the formula (III) with the compound of the formula (IV) in the presence of an alkali metal tert-butoxide (e.g. potassium tert-butoxide) or an alkali earth metal tert-butoxide, in tetrahydrofuran,
the pharmaceutically acceptable acid of the formula HA in step (iii) is L-malic acid.

Before converting the compound of the formula (I), wherein $R_1$–$R_4$ are hydrogen, into the L-malate salt, the product of the formula (V) is preferably converted to the fumarate, giving a more pure product. After that, the fumarate may be converted to the L-malate, e.g. via neutralization of the fumarate with a base and then converted to the L-malate by means of L-malic acid.

When $R_1$–$R_3$ are hydrogen and $R_4$ is ethoxy, it is preferred that:
step (i) is performed by reacting the hydrochloride of the compound of the formula (II) with 2-chloroethanol within an aqueous solution of a hydroxide, more preferably sodium hydroxide,
step (ii) is performed by reacting the compound of the formula (III) with the compound of the formula (IV) in the presence of an alkali metal tert-butoxide (e.g. potassium tert-butoxide) or an alkali earth metal tert-butoxide, in a solvent system consisting of methyl tert-butylether and tetrahydrofuran,
the pharmaceutically acceptable acid of the formula HA in step (iii) is succinic acid.

When $R_1$–$R_3$ are hydrogen and $R_4$ is 2-dimethylaminoethoxy, it is preferred that:
step (i) is performed by reacting the compound of the formula (II) with ethylene carbonate with an alkali metal carbonate (e.g. potassium carbonate) or an alkali earth metal carbonate, as a base and dimethyl sulfoxide as a solvent,
step (ii) is performed by reacting the compound of the formula (III) with the compound of the formula (IV) in the presence of an alkali metal tert-butoxide (e.g. potassium tert-butoxide) or an alkali earth metal tert-butoxide, in tetrahydrofuran,
the pharmaceutically acceptable acid of the formula HA in step (iii) is phosphoric acid.

This invention also features a process for the preparation of compounds of the general formula (I). The process includes the steps of:
(i) reacting a 3-pyridinol derivative of the general formula (II) or the corresponding hydrochloride with ethylene carbonate, to give another 3-pyridinol derivative of the general formula (III):
(ii) reacting the 3-pyridinol derivative of the general formula (III) with (2R)-1-(3-chloro-2-pyrazinyl)-2-methylpiperazine of the formula (IV) in the presence of an alkali metal tert-butoxide (e.g., potassium tert-butoxide) or an alkali earth metal tert-butoxide, to give a compound of the general formula (V),
(iii) converting the compound of the general formula (V) to the compund of the general formula (I) by treatment with a pharmaceutically acceptable acid of the formula HA (e.g., L-malic acid), wherein each of $R_1$, $R_2$, $R_3$, and $R_4$ is hydrogen. Step (i) can be performed in the presence of an alkali metal carbonate (e.g. potassium carbonate) or an alkali earth metal carbonate as a base, and dimethyl formamide as a solvent; and step (ii) can be performed by reacting the compound of the general formula (III) with the compound of the formula (IV) in tetrahydrofuran.

In this process, (2R)-1-(3-chloro-2-pyrazinyl)-2-methylpiperazine of the formula (IV) can be prepared by:
(iv) acidification of racemic 2-methylpiperazine of the formula (VI) with L-tartaric acid and fractional crystallization to give (R)-2-methylpiperazine, L-tartrate of the formula (VII):
(v) basification of (2R)-2-methylpiperazine, L-tartrate of the formula (VII) to give (R)-2-methylpiperazine of the formula (VIII):

(vi) tritylation of (R)-2-methylpiperazine of the formula (VIII) to give (R)-3-methyl-1-tritylpiperazine of the formula (IX), (vii) condensation of (R)-3-methyl-1-tritylpiperazine of the formula (IX) with 2,3-dichloropyrazine to give (2R)-1-(3-chloro-2-pyrazine)-2-methyl-4-tritylpiperazine of the formula (X):

(viii) detritylation of (2R)-1-(3-chloro-2-pyrazinyl)-2-methyl-4-tritylpiperazine of the formula (X) to give (2R)-1-(3-chloro-2-pyrazinyl)-2-methylpiperazine of the formula (IV), (ix) and conversion of (2R)-1-(3-chloro-2-pyrazinyl)-2-methylpiperazine of the formula (IV) to a suitable acid addition salt (e.g, hydrochloride salt).

The formula (I) to (X) are the same as described above.

This invention further features a process for the preparation of compounds of the general formula (I). The process includes the steps of:

(i) O-alkylating a 3-pyridinol derivative of the general formula (II) or the corresponding hydrochloride, to give another 3-pyridinol derivative of the general formula (III), (ii) reacting the 3-pyridinol derivative of the general formula (III) with (2R)-1-(3-chloro-2-pyrazinyl)-2-methylpiperazine of the formula (IV) in the presence of potassium tert-butoxide, to give a compound of the general formula (V), (iii) converting the compound of the general formula (V) to the compound of the general formula (I) by treatment with a pharmaceutically acceptable acid of the formula HA (e.g., succinic acid), wherein each of $R_1$, $R_2$, and $R_3$ is hydrogen, $R_4$ is $C_1$–$C_6$-alkoxy (e.g., ethoxy). Step (i) can be performed by reacting the hydrochloride of the compound of the general formula (II) with 2-chloroethanol in an aqueous solution of a hydroxide (e.g., sodium hydroxide), and step (ii) can be performed by reacting the compound of the general formula (III) with the compound of the formula (IV) in a solvent system consisting of methyl tert-butylether and tetrahydrofuran.

This invention also features a process for the preparation of compounds of the general formula (I). The process includes the steps of:

(i) reacting a 3-pyridinol derivative of the general formula (II) or the corresponding hydrochloride with ethylene carbonate, to give another 3-pyridinol derivative of the general formula (III):

(ii) reacting the 3-pyridinol derivative of the general formula (III) with (2R)-1-(3-chloro-2-pyrazinyl)-2-methylpiperazine of the formula (IV) in the presence of an alkali metal tert-butoxide (e.g., potassium tert-butoxide) or an alkali earth metal tert-butoxide, to give a compound of the general formula (V), (iii) converting the compound of the general formula (V) to the compund of the general formula (I) by treatment with a pharmaceutically acceptable acid of the formula HA (e.g., phosphoric acid), wherein each of $R_1$, $R_2$, and $R_3$ is hydrogen, $R_4$ is di-$C_1$–$C_6$-alkylamino-$C_2$–$C_6$-alkoxy (e.g., 2-dimethylaminoethoxy). Step (i) can be performed in the presence of an alkali metal carbonate (e.g. potassium carbonate) or an alkali earth metal carbonate as a base, and dimethyl sulfoxide as a solvent; and step (ii) can be performed by reacting the compound of the general formula (III) with the compound of the formula (IV) in tetrahydrofuran.

Another object of the present invention is a process for preparing (2R)-1-(3-chloro-2-pyrazinyl)-2-methylpiperazine, hydrochloride by reacting (2R)-1-(3-chloro-2-pyrazinyl)-2-methylpiperazine of the formula (IV) with hydrochloric acid.

Another object of the present invention is the compound (2R)-1-(3-chloro-2-pyrazinyl)-2-methylpiperazine, hydrochloride.

Another object of the present invention is a compound of the formula (I), wherein $R_1$–$R_4$ are hydrogen and HA is L-malic acid.

Another object of the present invention is a compound of the formula (I), wherein $R_1$–$R_3$ are hydrogen, $R_4$ is ethoxy and HA is succinic acid. Another object of the present invention is a compound of the formula (I), wherein $R_1$–$R_3$ are hydrogen, $R_4$ is 2-dimethylaminoethoxy, and HA is phosphoric acid.

Also within the scope of this invention is a method for the treatment or prophylaxis of a serotonin-related disorder, particularly 5-$HT_{2c}$ receptor related. The method includes administering to a subject in need thereof an effective amount of a compound of the formula (I), wherein $R_1$–$R_3$ are hydrogen, $R_4$ is selected from hydrogen, ethoxy, and 2-dimethylaminoethoxy, and HA is selected from L-malic acid, succinic acid, and phosphoric acid. Examples of such disorders are obesity and type II diabetes.

Also within the scope of this invention is the use of a compound of formula (I), wherein $R_1$–$R_3$ are hydrogen, $R_4$ is selected from hydrogen, ethoxy, and 2-dimethylaminoethoxy, and HA is selected from L-malic acid, succinic acid, and phosphoric acid, to manufacture a medicament for the treatment or prophylaxis of a serotonin-related disorder, particularly 5-$HT_{2c}$ receptor related. Examples of such disorders are obesity and type II diabetes.

Another aspect is a method of making a composition comprising combining a compound of formula (I) (including those made by the processes delineated herein) with a pharmaceutically acceptable carrier.

DETAILED DESCRIPTION OF THE INVENTION

Below, the various terms used in the above definition of the compounds of the compounds of the general formulas (I)–(V) will be explained.

$C_1$–$C_6$-alkyl is a straight or branched alkyl group having 1–6 carbon atoms. Exemplary alkyl groups include methyl, ethyl, n-propyl, isopropyl, n-butyl, sec-butyl, tert-butyl, n-pentyl, isopentyl, n-hexyl, and isohexyl.

For parts of the range "$C_1$–$C_6$-alkyl" all subgroups thereof are contemplated such as $C_1$–$C_5$-alkyl, $C_1$–$C_4$-alkyl, $C_1$–$C_3$-alkyl, $C_1$–$C_2$-alkyl, $C_2$–$C_6$-alkyl, $C_2$–$C_5$-alkyl, $C_2$–$C_4$-alkyl, $C_2$–$C_3$-alkyl, $C_3$–$C_6$-alkyl, $C_4$–$C_5$-alkyl, etc.

$C_1$–$C_6$-alkoxy is a straight or branched alkyl group having 1–6 carbon atoms. Exemplary alkoxy groups include methoxy, ethoxy, n-propoxy, isopropoxy, n-butoxy, sec-butoxy, tert-butoxy, n-pentoxy, isopentoxy, n-hexoxy, and isohexoxy.

For parts of the range "$C_1$–$C_6$-alkoxy" all subgroups thereof are contemplated such as $C_1$–$C_5$-alkoxy, $C_1$–$C_4$-alkoxy, $C_1$–$C_3$-alkoxy, $C_1$–$C_2$-alkoxy, $C_2$–$C_6$-alkoxy, $C_2$–$C_5$-alkoxy, $C_2$–$C_4$-alkoxy, $C_2$–$C_3$-alkoxy, $C_3$–$C_6$-alkoxy, $C_4$–$C_5$-alkoxy, etc.

The term "DSC" in the present description means "differential scanning calorimetry".

The term "DVS" in the present description means "dynamic vapor sorption gravimetry".

The term "FBE" in the present description means "free base equivalents".

The term "halogen" in the present description is intended to include fluorine, chlorine, bromine and iodine.

The term "IDR" in the present description means "intrinsic dissolution rate".

The term "IP" in the present description means "in process".

The term "NLT" in the present description means "not less than".

"Pharmaceutically acceptable acid salts" mean salts which are pharmaceutically acceptable, as defined above, and which possess the desired pharmacological activity. Such salts include acid addition salts formed with any organic and inorganic pharmaceutically acceptable acid ("HA"), such as hydrogen chloride, hydrogen bromide, hydrogen iodide, sulfuric acid, phosphoric acid, acetic acid, glycolic acid, maleic acid, malonic acid, oxalic acid, toluenesulfonic acid, methanesulfonic acid, trifluoroacetic acid, fumaric acid, succinic acid, malic acid, tartaric acid, citric acid, benzoic acid, ascorbic acid and the like.

DMF means dimethyl formamide, DMSO means dimethyl sulfoxide, IPA means isopropanol, MtBE means methyl tert-butyl ether, RH means relative humidity, RT means room temperature, t-BuOK means tert-butyl alcohol, potassium salt, THF means tetrahydrofuran, and trityl means triphenylmethyl.

It should be noted that both E- and Z-isomers of the compounds, optical isomers, as well as mixtures thereof, and all isotopes are included within the scope of the invention. By the expression "isotopes" is meant all compounds with naturally occurring isotopes such as all possible deuterium and $^{13}C$-isotopes of the compounds according to the invention. The compounds of the present invention may also contain unnatural proportions of atomic isotopes at one or more of the atoms that constituted such compounds. For example, the compounds may be radiolabelled with radioactive isotopes, such as fore example tritium ($^3H$), $^{125}I$ or $^{14}C$. All isotopic variations of the compounds of the present invention, whether radioactive or not, are intended to be encompassed within the scope of the present invention.

The chemicals used in the above-described synthetic routes may include, for example, solvents, reagents, catalysts, protecting group and deprotecting group agents. The methods described above may also additionally include steps, either before or after the steps described specifically herein, to add or remove suitable protecting groups in order to ultimately allow synthesis of the compounds of the formula (I). Synthetic chemistry transformations and protecting group methodologies (protection and deprotection) useful in synthesizing applicable compounds of the formula (I) are known in the art and include, for example, those described in R. Larock, *Comprehensive Organic Transformations*, VCH Publishers (1989); T. W. Greene and P. G. M. Wuts, *Protective Groups in Organic Synthesis*, $2^{nd}$ Ed., John Wiley and Sons (1991); L. Fieser and M. Fieser, *Fieser and Fieser's Reagents for Organic Synthesis*, John Wiley and Sons (1994); and L. Paquette, ed., *Encyclopedia of Reagents for Organic Synthesis*, John Wiley and Sons (1995) and subsequent editions thereof.

In accordance with the present invention, the compound of the formula (I), wherein $R_1$–$R_3$ are hydrogen, $R_4$ is selected from hydrogen, ethoxy or 2-dimethylaminoethoxy and HA is selected from L-malic acid, succinic acid, and phosphoric acid, can be brought into suitable galenic forms, such as compositions for oral use, for injection, for nasal spray administration or the like, in accordance with accepted pharmaceutical procedures. Such pharmaceutical compositions according to the invention comprise an effective amount of the aforementioned compound in association with compatible pharmaceutically acceptable carrier materials, or diluents, as are well known in the art. The carriers may be any inert material, organic or inorganic, suitable for enteral, percutaneous, subcutaneous or parenteral administration, such as: water, gelatin, gum arabicum, lactose, microcrystalline cellulose, starch, sodium starch glycolate, calcium hydrogen phosphate, magnesium stearate, talcum, colloidal silicon dioxide, and the like. Such compositions may also contain other pharmacologically active agents, and conventional additives, such as stabilizers, wetting agents, emulsifiers, flavouring agents, buffers, and the like.

The compositions according to the invention can e.g. be made up in solid or liquid form for oral administration, such as tablets, pills, capsules, powders, syrups, elixirs, dispersable granules, cachets, suppositories and the like, in the form of sterile solutions, suspensions or emulsions for parenteral administration, sprays, e.g. a nasal spray, transdermal preparations, e.g. patches, and the like.

As mentioned above, the aforementioned compounds of the invention may be used for the treatment or prophylaxis of a subject (e.g., a human or an animal) suffering from a serotonin-related disorder or conditions, particularly 5-$HT_{2c}$ receptor related, such as memory disorders, such as Alzheimer's disease; schizophrenia; mood disorders such as depression; anxiety disorders; pain; substance abuse; sexual dysfunctions such as erectile dysfunction; epilepsy; glaucoma; urinary disorders, such as urinary incontinence; menopausal and post-menopausal hot flushes; eating disorders, such as binge eating disorders, anorexia nervosa and bulimia; weight gain associated with antipsychotic drug administration, type II diabetes; and particularly obesity.

The method of treatment or prophylaxis includes administering to a subject in need of treatment an effective amount of the compound of this invention. The term "treating" or "treated" refers to administering a compound of this invention to a subject with the purpose to cure, heal, alleviate, relieve, alter, remedy, ameliorate, improve, or affect a disease, the symptoms of the disease or the predisposition toward the disease. "An effective amount" refers to an amount of a compound which confers a therapeutic effect on the treated subject. The therapeutic effect may be objective (i.e., measurable by some test or marker) or subjective (i.e., subject gives an indication of or feels an effect). The dose level and frequency of dosage of the specific compound will vary depending on a variety of factors including the potency of the specific compound employed, the metabolic stability and length of action of that compound, the patient's age, body weight, general health, sex, diet, mode and time of administration, rate of excretion, drug combination, the severity of the condition to be treated, and the patient undergoing therapy. The daily dosage may, for example, range from about 0.001 mg to about 100 mg per kilo of body weight, administered singly or multiply in doses, e.g. from about 0.01 mg to about 25 mg each. Normally, such a dosage is given orally but parenteral administration may also be chosen.

The invention also refers to the use of the aforementioned compounds to manufacture a medicament for the treatment or prophylaxis of a serotonin-related disorder, particularly 5-$HT_{2c}$ receptor related.

All publications mentioned herein are hereby incorporated by reference. By the expression "comprising" we understand including but not limited to.

The invention will now be illuminated by the following Examples, which are only intended to illuminate and not restrict the invention in any way. Examples 1A–3A illustrate steps (i)–(iii) when $R_1$–$R_4$ are hydrogen. Examples 1B–3B illustrate steps (i)–(iii) when $R_1$–$R_3$ are hydrogen and $R_4$ is ethoxy. Examples 1C–3C illustrate steps (i)–(iii) when $R_1$–$R_3$ are hydrogen and $R_4$ is 2-dimethylaminoethoxy. Examples 4–8 illustrate steps (iv)–(viii) when $R_1$–$R_3$ are hydrogen and $R_4$ is selected from the group consisting of hydrogen, ethoxy, and 2-dimethylaminoethoxy. Regarding the compound of the formula (IV) as prepared in step (viii), it has been shown that this compound is not stable for storage as a free base. However, the corresponding hydrochloride thereof is considerably more stable. Example 9 describes the preparation of (2R)-1-(3-chloro-2-pyrazinyl)-2-methylpiperazine, hydrochloride. Furthermore, the properties of different salts of the formula (I) were evaluated. Example 10 describes the preparation of (2R)-methyl-1-{3-[2-(3-pyridinyloxy)ethoxy]-2-pyrazinyl}piperazine, fumarate. By making the fumarate in Example 10, a more pure product is obtained before converting to the L-malate salt (prepared in Example 3A). Example 11 describes the comparison of the properties of different salts of Example 2A. Example 12 describes the comparison of the properties of different salts of Example 2B. Example 13 describes the comparison of the properties of different salts of Example 2C.

EXAMPLES

General 2-ethoxy-3-hydroxypyridine, HCl (for Example 1B) and 2-(2-dimethylaminoethoxy)pyridin-3-ol (for Example 1C) were purchased from Nordic Synthesis in Karlskoga, Sweden. The other chemicals mentioned are commercially available and could e g be purchased from Aldrich. For Examples 1B–3B, HPLC analysis confirmed that the desired products were obtained. The HPLC pump was a Varian 9012. A Varian 9050 detector at 220 nm was used. The eluent was 80 mM $KH_2PO_4$ in a 80:20 mixture of water/acetonitrile. The column was a Varian C8, 150×4.5 mm. For Examples, 1C–3C, HPLC analysis also confirmed that the desired products were obtained. The eluent was A: 0.1% trifluoroacetic acid in water, B: acetonitrile; increasing percentage of acetonitrile during 3 minutes. The column was a YMC FL-ODS AQ S-5μ, 12 nm, 50×4.6 mm (Example 1C) and a Hypersil BDS C18, 3μ, 30×4.6 mm (Example 2C–3C), respectively.

Example 1A

Preparation of 2-(3-pyridinyloxy)ethanol 3-hydroxypyridine (20.0 kg), ethylene carbonate (19.4 kg), $K_2CO_3$ (18.9 kg), and DMF (75.5 kg) were charged to a 400 L reactor and heated to 86° C. After 13 h, an aliquot was taken. There was still some 3-hydroxypyridine left by GC so more ethylene carbonate (1.0 kg) was added. After 20 h, the reaction was deemed complete. The reaction was cooled to 20° C., $H_2O$ (85 L) was slowly added to the 400 L reactor, and stirring continued for 30 min. The title compound was extracted with 35° C. $CH_2Cl_2$ (4×170 L) sending the $CH_2Cl_2$ extractions into the 1000 L portable tank. The aqueous layer was discarded, and the 400 L reactor was cleaned. The solution of the title compound in the 1000 L portable tank was transferred to the 400 L and distilled in the 400 L reactor sending the distillate to the 400 L receiver. Toluene (200 L) was added to the 400 L reactor and distilled sending the distillate to the 400 L receiver. The resulting oil was transferred to a 20 L glass bottle to produce 21.0 kg (72%) of the title compound of 100.0% GC purity.

The yield of the title compound according to D1, starting from 3-hydroxypyridine, 2-chloroethanol and $K_2CO_3$ in DMF was 19%. The title compound has also been prepared according to EP 0 286 242 A2 starting from methyl [(3-pyridinyl)oxy]acetate.

$^1$H NMR (400 MHz, $CDCl_3$): δ 8.30 (1H, br s), 8.20 (1H, t, J=3.1 Hz), 7.23 (2H, t, J=2.1 Hz), 4.13 (2H, t, J=4.6 Hz), 3.99 (2H, t, J=4.6 Hz), 3.76 (1H, br s), 0.00 (TMS, reference).

$^{13}$C NMR (100 MHz, $CDCl_3$): δ 155.09 (s), 142.09 (d), 137.95 (d), 123.99 (d), 121.32 (d), 69.83 (t), 60.98 (t), 0.00 (TMS, reference).

IR (liq.) 2382 (w), 2082 (w), 1996 (w), 1954 (w), 1587, 1576 (s), 1488, 1478 (s), 1429 (s), 1272 (s), 1235 (s), 1084, 1054 (s), 802, 707 (s), $cm^{-1}$.

Anal. Calcd for $C_7H_9NO_2$: C, 60.42; H, 6.52; N, 10.07. Found: C, 60.14; H, 6.51; N, 10.39.

HRMS (FAB) calcd for $C_7H_9NO_2+H_1$ 140.0712, found 140.0705.

Example 1B

Preparation of 2-[(2-ethoxy-3-pyridinyl)oxy]ethanol

To water (30.0 kg) was added 3.40 kg of NaOH. The resulting suspension was stirred until complete dissolution had occurred. The temperature of the solution was then adjusted to approx. 60° C. To the alkaline solution was carefully added 2-ethoxy-3-hydroxypyridine, HCl (6.00 kg). The temperature was raised to 85.0° C. and the mixture stirred for 30 min to allow for complete dissolution. During 85 min, 2-chloroethanol (4.10 kg) was added, while the temperature was kept between 88.0–92.0° C. The reaction was allowed to age for 50 min at approx. 90° C., after which time HPLC indicated complete conversion of 2-ethoxy-3-hydroxypyridine, HCl to the title compound. The reaction mixture was poured into 65.1 kg of methyl tert-butylether (MtBE). The reaction vessel was rinsed with water (2.0 kg). To the resulting two-phase system was added 3.05 kg of NaCl and 0.20 kg of NaOH. The resulting mixture was stirred for 55 min, while the temperature was lowered to 24.9° C. The mixture was the allowed to stir for another 20 min at 23.7–24.9° C. The water phase was removed. The remaining organic phase was concentrated by distillation at atmospheric pressure. When 45 L had been removed, the residue was cooled to room temperature and transferred to a drum. The residue weighed 33.1 kg. According to HPLC, the assay is 118.9 g of the title compound per kg of mixture, corresponding to a yield of 6.25 kg (quantitative yield) of pure title compound.

The yield of the title compound according to Dl, starting from 2-bromo-3-(2-{[tert-butyl(dimethyl)silyl]oxy}ethoxy) pyridine and sodium ethoxide in ethanol was 41%.

Example 1C

Preparation of 2-{[2-(2-dimethylaminoethoxy)-3-pyridinyl]oxy}ethanol

DMSO (17 L) and potassium carbonate (8.2 kg) were charged to the 100 L-glasslined reactor. The mixture was heated to 58° C. while stirring. 2-(2-Dimethylaminoethoxy) pyridin-3-ol (4.11 kg) was charged to the reactor during 25 minutes (gas evolution). The mixture was heated to 117° C. before the prepared ethylene carbonate solution was added through the manhood in portions. After 1 L ethylene carbonate solution was added IP-HPLC was taken to ensure that the title compound had started to form. The total addition of ethylene carbonate solution was made during 1 h 35 minutes. Temperature after the addition was 124° C. A HPLC sample was taken from the reaction mixture 10 minutes after finished addition. It showed 95% conversion to product. The reaction-mixture was allowed to cool to 70° C. before water (45 L) and sodium chloride (4.06 kg) was charged to the reactor. The mixture was then stirred for 20 minutes at 70° C. before cooled to RT. Ethyl acetate (137 L) was charged into a 328 L glass-lined reactor. The water mixture was transferred from the 100 L reactor to the 328 L reactor. The mixture was stirred for 25 minutes before the mechanical stirrer was turned off. After allowing the phases to separate for 40 minutes, the water-phase (65 L) was discharged. The mixture was heated to reflux and 102 L of ethyl acetate was distilled off. Toluene (72 L) was added and the mixture was heated to reflux again and 61 L of toluene/ethyl acetate was distilled off. The reaction mixture was then cooled to RT. The title compound was never isolated; it was directly used in Example 2C.

The preparation of the title compound has not been described in D1.

Example 2A

Preparation of (2R)-methyl-1-{3-[2-(3-pyridinyloxy)ethoxy]-2-pyrazinyl}piperazine A 400 L reactor containing a toluene solution of (2R)-1-(3-chloro-2-pyrazinyl)-2-methylpiperazine (for preparation of this compound, see Example 8 below) was distilled to remove toluene. THF (40 kg) was added, and the slurry was stirred until all the oil dissolved. The solution was transferred to a drum with a THF rinse (10 kg). The THF/toluene solution of (2R)-1-(3-chloro-2-pyrazinyl)-2-methylpiperazine (ca 9.7 kg thereof in 90.4 kg solution) was transferred to a 1200 L reactor with a THF rinse (4 L). 2-(3-pyridinyloxy)ethanol from Example 1A (7.6 kg) was transferred to the 1200 L reactor with a THF rinse (34 L) and stirred at room temperature for 15 min. 20 wt % KOt-Bu (33.3 kg) was added followed by a THF rinse (4 kg). The reaction was monitored by GC and was complete in 15 min. The reaction in the 1200 L reactor was quenched with $H_2O$ (119 L) and extracted with $CH_2Cl_2$ (1×215 L, 2×117 L) sending the $CH_2Cl_2$ extractions into the 800 L receiver. The $CH_2Cl_2$ solution was transferred to the 1200 L reactor and the $CH_2Cl_2$ was removed by distillation. A solvent swap distillation using MeOH (2×215 L) was performed distilling to a volume of 100 L. The MeOH solution of the title compound was filtered through a bag filter containing carbon (5 kg) recycling the solution four times from the 1200 L reactor to the 800 L receiver. The solution in the 800 L receiver was transferred to the 1200 L reactor with a MeOH rinse (50 L). The solution was distilled to a final volume of 70 L and transferred to a drum with a MeOH rinse (10 L) in preparation for the compound in Example 3A. The yield was quantitative.

The yield of the hydrochloride of the title compound according to D1, starting from 3-chloro-2-[4-tert-butoxycarbonyl-(2R)-methyl-1-piperazinyl]pyrazine and 2-(3-pyridinyloxy)ethanol with potassium tert-butoxide in dioxane was 31%.

$^1$H NMR (400 MHz, CDCl$_3$): δ 8.35 (1H, br s), 8.25 (1H, t, J=3.0 Hz), 7.74 (1H, d, J=3.0 Hz), 7.49 (1H, d, J=2.5 Hz), 7.23 (2H, br t, J=2.3 Hz), 4.76 (1H, dt, J=12.2, 4.8 Hz), 4.67 (1H, dt, J=11.7 Hz, 5.2 Hz), 4.49–4.43 (1H, m), 4.40 (2H, t, J=4.8 Hz), 3.72 (1H, br d, J=12.8 Hz), 3.27 (1H, td, J=11.7, 3.0 Hz), 3.06 (1H, dd, J=12.3, 3.6 Hz), 2.99 (1H, br d, J=12.2 Hz), 2.88 (1H, td, J 11.7, 3.4 Hz), 2.75 (1H, br d, J=12.3 Hz), 1.72 (1H, br s), 1.19 (3H, d, J=6.6 Hz), 0.00 (TMS, reference).

$^{13}$C NMR (100 MHz, CDCl$_3$): δ 154.86 (s), 150.35 (s), 147.30 (s), 142.60 (d), 138.09 (d), 134.14 (d), 129.89 (d), 123.87 (d), 121.17 (d), 66.54 (t), 63.97 (t), 50.86 (t), 49.52 (d), 46.22 (t), 42.78 (t), 14.26 (q), 0.00 (TMS, reference).

IR (liq.) 2068 (w), 1996 (w), 1576 (s), 1528 (s), 1475 (s), 1430 (s), 1330 (s), 1276 (s), 1268 (s), 1246, 1208 (s), 1187 (s), 1181 (s), 1063, 708, cm$^{-1}$.

HRMS (FAB) calcd for $C_{16}H_{21}N_5O_2+H_1$ 316.1773, found 316.1777.

$[α]^{25}_D=-24°$ (c 0.92, water).

Anal. Calcd for $C_{16}H_{21}N_5O_2$: C, 60.94; H, 6.71; N, 22.21. Found: C, 59.98; H, 6.73; N, 22.40.

Example 2B

Preparation of (2R)-1-(3-[2-[(2-ethoxy-3-pyridinyl)oxy]ethoxy]-2-pyrazinyl)-2-methylpiperazine (2R)-1-(3-chloro-2-pyrazinyl)-2-methylpiperazine (9.00 kg) (see Example 8 for preparation) was dissolved in 20.1 kg of water by stirring a room temperature for 25 min. Activated charcoal (0.50 kg) and celite (0.50 kg) was added. The resulting suspension was stirred for 30 min at room temperature. The charcoal and celite was removed by filtration under pressure. The filtered water-phase was poured into 63.9 kg of MtBE (methyl tert-butylether). To the resulting two-phase system were added NaOH (1.50 kg) and NaCl (4.40 kg). After stirring for 25 min at room temperature, the water phase was discarded. The remaining organic phase was concentrated by distillation at atmospheric pressure. A total of 45 L was removed. To the remaining content of the reactor was added an MtBE-solution of 2-[(2-ethoxy-3-pyridinyl)oxy]ethanol (one complete batch from Example 1B). The resulting mixture is concentrated by distillation at atmospheric pressure. A total of 40 L was removed. To the residue, 40.8 kg of MtBE was added. Further concentration by distillation was done with a total of 20 L being removed. A solution of potassium tert-butoxide (KtBuO) was made by suspending 2.96 kg of KtBuO in 13.1 kg of THF. After stirring for 30 min at room temperature almost everything was in solution. After emptying the reactor, a second solution was made by in a similar way (3.02 kg of KtBuO to 13.0 kg of THF). The mixture of 2-[(2-ethoxy-3-pyridinyl)oxy]ethanol and (2R)-1-(3-chloro-2-pyrazinyl)-2-methylpiperazine was heated to 51.0° C. To this mixture was added the solutions of KtBuO in THF. During the addition, the temperature was kept between 50.7–55.6° C. The total addition time was 50 min. After aging for 35 min at 55° C., HPLC indicated that the reaction was complete. The reaction mixture was cooled to room temperature and 23.1 kg of water was cautiously added while maintaining the temperature below 25° C. After stirring for 15 min at approx. 23° C., the water phase was discarded. The remaining organic phase was concentrated by distillation at atmospheric pressure. After 45 L had been removed, heptane (38.0 kg) was added. Further distillation removed 50 L, followed by addition of heptane (33.8 kg). By removing another 30 L via distillation, all remaining MtBE had been removed from the heptane solution. To the residue, 20.8 kg of water was added and the temperature raised to 72.8° C. After stirring for 15 min, the water phase was removed at this temperature. The remaining solution was concentrated by distillation at atmospheric pressure. A total of 50 L was removed. The residue was cooled to 50.5° C. The solution was seeded with 5.0 g of the title compound to induce crystallization. The resulting suspension was stirred at 51.5° C. for 35 min while maintaining maximum stirring speed. Cooling was then continued to 8.1° C. over night. The product was isolated via filtration under suction. The resulting product cake was washed with 11 L of heptane. The semi-dry cake weighing 9.63 kg was dried at 40° C./vakuum. The dried product weighed 8.1 kg (66%).

The yield of the fumarate of the title compound according to D1, starting from (2R)-1-(3-chloro-2-pyrazinyl)-2-methylpiperazine and 2-[(2-ethoxy-3-pyridinyl)oxy]ethanol with sodium tert-butoxide in dioxane was 17%.

Example 2C

Preparation of (2R)-1-[3-(2-{[2-(2-dimethylaminoethoxy)-3-pyridinyl]oxy}ethoxy)-2-pyrazinyl]-2-methylpiperazine (2R)-1-(3-chloro-2-pyrazinyl)-2-methylpiperazine (20 L in toluene solution; see Example 8 for preparation) and active charcoal (201 g) was added to the 328 L-reactor containing 2-{[2-(2-dimethylaminoethoxy)-3-pyridinyl]oxy} ethanol (Example 1C) in toluene solution. The mixture was stirred for 25 minutes before transferred to a through a GAF-filter (containing a Teflon filter bag) to a 250 L-stainless steel reactor. The mixture was heated to 100° C. before the prepared "THF/potassium tert-butoxide-solution" was added to the reactor using a 50 L addition bowl. After 10 L "THF/potassium tert-butoxide-solution" was added, an IP-HPLC was taken to ensure that the title compound had started to form. The total addition of THF/potassium tert-butoxide-solution was made during 2 h and 15 minutes. Water (21 L) and sodium chloride (1 kg) was added to a 198 L-glasslined reactor. The salt was dissolved before the reaction mixture was transferred from the 328 L-reactor and quenched into the 198 L-reactor. Toluene (10 L) was also transferred to make sure that no reaction-mixture was left in the hoses used for the transfer. The mixture was then heated to 70° C. before the mechanical stirrer was turned off. The phases were allowed to separate for 30 minutes before the water phase (25 L) was discharged. The mixture was heated to reflux and toluene (10 L) was distilled off. Water (100 L) was added and the mixture was heated to reflux again and 60 L of water was distilled off. The remaining solution was then cooled to RT. The title compound was never isolated; it was directly used in the next step (Example 3C). IP sample (HPLC) of the toluene mixture confirmed the retention time for the desired product ($t_{ret}$=2.2 minutes).

The preparation of the title compound has not been described in D1.

Example 3A

Preparation of (2R)-methyl-1-[3-[2-(3-pyridinyloxy) ethoxy]-2-pyrazinyl]piperazine, L-malate Salt To a 120 L receiver was added (2R)-methyl-1-{3-[2-(3-pyridinyloxy)ethoxy]-2-pyrazinyl}piperazine from Example 2A (4.09 kg) and MeOH (12.7 kg) with stirring for about 7 min until all substance had dissolved. The solution was transferred to the 120 L reactor through an in-line filter followed by a MeOH (2 kg) rinse. The L-malic acid (1.79 kg) was added to the 120 L receiver followed by acetone (8.8 kg) with stirring for about 13 min until all the L-malic acid had dissolved. The solution was transferred to the 120 L reactor through an in-line filter followed by an acetone (2 kg) rinse. The solution in the 120 L reactor was cooled to 5° C. MtBE (25 kg) was added to the 120 L receiver and slowly transferred through an in-line filter into the 120 L reactor. The solution was stirred at 0° C. for 1 h and filtered onto the 18" nutsche sending the filtrate into the 120 L receiver. (Inspection showed little product in the nutsche; only small amounts of oil were present.) MeOH (40 L) was added to the 18" nutsche to dissolve the oil. The MeOH solution and the filtrate in 120 L receiver were transferred through an in-line filter into 120 L reactor and the solution was distilled to a solid sending the distillate to the 120 L receiver, which was disposed. MeOH (I 5 kg) was added through an in-line filter to 120 L reactor. The solution in 120 L reactor was distilled atmospherically replacing the MeOH with EtOH (35 kg) to a volume of 15 L. The solution was cooled to 58.6° C., seeded with 10 g of (2R)-methyl-1-{3-[2-(3-pyridinyloxy) ethoxy]-2-pyrazinyl}piperazine, L-malate salt, and cooling continued to 25° C. Stirring was continued for 24 h, and the resulting slurry was filtered onto the 18" nutsche sending the filtrate into the 120 L receiver. The filter cake on the 18" nutsche was rinsed with filtered EtOH (15 kg) sending the rinse into the 120 L receiver. The title compound was dried under vacuum using 60° C. nitrogen, deagglomerated, and packaged to yield 3.58 kg (61%) of the title compound of 98.61% GC purity.

The preparation of the title compound has not been described in D1.

M.Pt. 124.5–126.6° C.

$^1$H NMR (400 MHz, d$_4$-MeOH): δ 8.28 (1H, d, J=2.6 Hz), 8.16 (1H, d, J=4.6 H (1H, d, J=2.5 Hz), 7.65 (1H, d, J=3.0 Hz), 7.49 (1H, dd, J=8.6, 2.5 Hz), 7.38 (1H, dd, J=8.3, 4.8 Hz), 4.78–4.73 (2H, m), 4.65 (1H, quintet, J=3.4 Hz), 4.48 (2H, t, J=4.4 Hz), 4.29 (1H, dd, J=7.3, 5.3 Hz), 3.98 (1H, dt, J=14.3, 3.1 Hz), 3.50 (1H, ddd, J=14.3, 11.2, 2.6 Hz), 3.31 (d$_4$-MeOH), 3.30–3.24 (2H, m), 3.21–3.15 (2H, m), 2.77 (1H, dd, J=15.8, 5.1 Hz), 2.53 (1H, dd, J=15.8, 7.1 Hz), 1.28 (3H, d, J=7.1 Hz, 0.00 (TMS, reference).

$^{13}$C NMR (100 MHz, d$_4$-MeOH): δ 179.64 (s), 176.38 (s), 157.02 (s), 152.32 (s), 147.25 (s), 142.72 (d), 138.58 (d), 135.14 (d), 133.35 (d), 125.97 (d), 123.40 (d), 69.67 (d), 68.00 (t), 65.78 (t), 48.61 (d), 48.32 (t), 44.31 (t), 41.84(t), 40.20 (t), 14.80 (q), 0.00 (TMS, reference).

IR (diffuse reflectance) 3030 (s), 3009, 2970, 2469 (b), 2358, 2342 (b), 2318 (b), 2303, 1571 (s), 1471, 1449, 1408, 1275 (s), 1233 (s), 1206 (s), cm$^{-1}$.

HRMS (FAB) calcd for $C_{16}H_{21}N_5O_2+H_1$ 316.1773, found 316.1780.

$[α]^{25}$D=−21° (c 0.98, water).

Anal. Calcd for $C_{16}H_{21}N_5O_2 \cdot C_4H_6O_5$: C, 53.44; H, 6.05; N, 15.58. Found: C, 53.23; H, 6.08; N, 15.29.

Example 3B

Preparation of (2R)-1-(3-{2-[(2-ethoxy-3-pyridinyl) oxy]ethoxy}-2-pyrazinyl)-2-methylpiperazine, Succinate Salt (2R)-1-(3-{2-[(2-ethoxy-3-pyridinyl)oxy]ethoxy}-2-pyrazinyl)-2-methylpiperazine (8.00 kg) obtained in Example 2B was dissolved in 24.0 kg of 1-propanol by heating to 60.5° C. The undissolved material was removed by filtration. Succinic acid (1.30 kg) was dissolved in 23.9 kg of 1-propanol by heating to 60.6° C. All undissolved material was removed by filtration. The procedure was repeated once with another 1.30 kg of succinic acid and 23.9 kg of 1-propanol. All of the above solutions were mixed in a reactor. After mixing, the content's temperature was 53.9° C. The solution was heated to 78.3° C. Cooling was applied. At 40.3° C., seeding with the title compound was done. Crystallization started after the seeding. The contents were stirred, while the temperature was lowered to 18.3° C. during the night. The product was isolated via filtration under suction. The resulting product cake was washed with 10 L of 1-propanol. The resulting semi-dry cake, weighing 17.2 kg was dried at 50° C./vakuum. After drying, the product, the title compound weighed 9.16 kg (86%).

The preparation of the title compound has not been described in D1.

Melting temperature onset, 123° C.; thermal melting range, 116–132° C.

$^1$H NMR (500 MHz, DMSO-d$_6$): δ 1.12 (d, J=6.8 Hz), 1.28 (t, J=7.1 Hz), 2.34 (s), 2.79 (m), 2.79 (m), 2.95 (m), 2.95 (m), 3.20 (dddd, J=13.7, 11.5, 3.0, 1.1 Hz), 3.77 (dt, J=3.0, 13.7 Hz), 4.30 (q, J=7.1 Hz), 4.37 (strong coupled), 4.49 (dqd, J=7.0, 6.8, 3.1 Hz), 4.62 (strong coupled), 6.89 (dd, J=5.0, 7.8 Hz), 7.33 (dd, J=1.5, 7.8 Hz), 7.58 (d, J=2.8 Hz), 7.69 (dd, J=1.5, 5.0 Hz), 7.77 (d, J=2.8 Hz).

$^{13}$C-NMR (500 MHz, DMSO-d$_6$): δ 14.2, 14.5, 30.5, 40.5, 44.0, 47.9, 48.4, 61.0, 64.0, 66.5, 116.8, 119.9, 130.3, 133.7, 137.2, 142.7, 146.3, 149.9, 153.8, 174.5.

Anal. Calcd for $C_{18}H_{25}N_5O_3 \cdot C_4H_6O_4$: C, 55.34%; H, 6.54%; N, 14.67%. Found: C, 54.86; H, 6.75%; N, 13.85%.

Example 3C

Preparation of (2R)-1-[3-(2-{[2-(2-dimethylamino-ethoxy)-3-pyridinyl]oxy}ethoxy)-2-pyrazinyl]-2-methylpiperazine, phosphoric acid salt (2R)-1-[3-(2-{[2-(2-dimethylaminoethoxy)-3-pyridinyl]oxy}ethoxy)-2-pyrazinyl]-2-methylpiperazine (Example 2C) in water solution was added to the 198 L-glasslined reactor and heated to reflux. Water (30 L) was removed by distillation. The mixture was cooled to RT. before active charcoal (403.5 g) was added. The mixture was stirred for 30 minutes before transferred to the 100 L glass-lined reactor using Teflon hose and a GAF-filter (containing a polypropylene filter bag) and a Millipore filter (containing a polyguard filter cartridge). The hoses and filters were rinsed with water (10 L). To the water solution in the 100 L reactor phosphoric acid (3.83 kg) was added. The mixture was heated to reflux and water was distilled off until an 18 L solution of (2R)-1-[3-(2-{[2-(2-dimethylaminoethoxy)-3-pyridinyl]oxy}ethoxy)-2-pyrazinyl]-2-methylpiperazine in water/phosphoric acid remained. Ethanol (71 L) was added to the solution while heating the mixture to reflux. All (2R)-1-[3-(2-{[2-(2-dimethylaminoethoxy)-3-pyridinyl]oxy}ethoxy)-2-pyrazinyl]-2-methylpiperazine was in solution before the heat was turned off and the mixture allowed to cool to RT. A small amount of the solution was taken out to create seeds and the reaction-mixture was seeded when the temperature was 60–68° C. The mixture was allowed to crystallize for 3 days (over a weekend, no cooling media was used) and the crystals were collected by filtration using a Teflon filter nutch. The crystals were then dried in a vacuum oven for 2 days at 60° C. and at 100–200 mbar. 4.5 kg of the title compound was isolated. IP sample (HPLC) of the title compound confirmed the retention time for the title compound (tret=$^{2.2}$ minutes). The yield of the title compound was 57% starting from 2-(2-dimethylaminoethoxy)pyridin-3-ol.

By starting from (2R)-1-[3-(2-{[2-(2-dimethylaminoethoxy)-3-pyridinyl]oxy}-ethoxy)-2-pyrazinyl]-2-methylpiperazine (Example 2C) with a purity of 60–70%, the title compound was obtained with a purity of 99% in one crystallization step.

The preparation of the title compound has not been described in D1.

Melting temperature onset, 148.0° C. (extrapolated); thermal melting range, 140–168° C.

$^1$H NMR (500 MHz, DMSO-d$_6$): δ 1.21 (d, J=7.0), 2.60 (s), 2.92 (td, J=12.2, 3.2 Hz), 3.02 (dd, J=13.0, 2.6 Hz), 3.08 (dd, J=13.0, 4.2 Hz), 3.16 (m), 3.17 (t, J=5.7 Hz), 3.38 (ddd, J=14.2, 11.6, 2.8 Hz), 3.94 (dt, J=14.2, 3.2 Hz), 4.40(m), 4.52(m), 4.59 (m), 4.61 (m), 4.67 (ddd, J=12.3, 5.1, 3.5 Hz), 6.96 (dd, J=7.8, 5.0 Hz), 7.39 (dd, J=7.8, 1.4 Hz), 7.62 (d, J=2.9 Hz), 7.71 (dd, J=5.0, 1.4 Hz), 7.80 (d, J=2.9 Hz).

$^{13}$C-NMR (400 MHz, DMSO-d$_6$): δ 14.3, 38.6, 42.2, 43.4, 46.2, 46.7, 55.5, 61.3, 64.0, 66.4, 117.7, 120.0, 130.9, 133.8, 137.0, 142.7, 145.7, 150.0, 152.8.

HRMS m/z calcd for $C_{20}H_{30}N_6O_3$ (M)+402.2379, found 402.2366.

Anal. Calcd for $C_{20}H_{30}N_6O_3 \cdot 3H_3PO_4$: C; 34.49%; H, 5.64%; N, 12.07%; O, 34.46%; P, 13.34%. Found: C, 37.20%; H, 6.0%; N, 12.5%; 0, 32.4%; P, 12.1%.

Example 4

Preparation of (R)-2-methylpiperazine, L-tartrate

To the 1200 L reactor was added 60° C. racemic 2-methylpiperazine (100 kg) from a drum. H$_2$O (240 L) was added, and the solution was cooled to 13° C. To the 1200 L receiver was added L-tartaric acid (150 kg). H$_2$O (140 L) was added, and the slurry was stirred for 1 h 35 min until dissolution of the solids was complete. The L-tartaric acid solution was transferred to the 1200 L reactor over 2 h while maintaining a temperature of 10–22° C. in the 1200 L reactor followed by a H$_2$O rinse (20 L). Ethanol (163 kg) was added to the 1200 L reactor, and the solution was cooled to 2° C. The resulting slurry was stirred for 2 h at 2° C., and filtered through a 36" Nutsche filter sending the filtrate into the 1200 L receiver. The 1200 L reactor and 36" Nutsche filter were washed with H$_2$O (200 L), and the solids were dried to yield 214 kg of 12% ee (171% based on the title compound). These solids were recharged to a clean 1200 L receiver and H$_2$O (630 L) was added to the 1200 L receiver, which was heated to 85° C. until all the solids had dissolved. The solution was filtered through an in-line filter (C) into the 1200 L reactor, cooled to 5° C., and stirred for 2 h. The resulting slurry was filtered through a clean 36" Nutsche filter sending the filtrate into the 1200 L receiver. The 1200 L reactor and 36" Nutsche filter were washed with H$_2$O (200 L), and the solids were dried to yield 104 kg of 93% ee (83% based on the title compound). These solids were recharged to a clean 1200 L receiver and H$_2$O (254 L) was added to the 1200 L receiver, which was heated to 85° C. until all the solids had dissolved. The solution was filtered through an in-line filter (C) into the 1200 L reactor, cooled to 5° C., and stirred for 2 h. The resulting slurry was filtered through a clean 36" Nutsche filter sending the filtrate into the 1200 L receiver. The 1200 L reactor and 36" Nutsche filter were washed with H$_2$O (200 L), and the solids were dried to yield 92 kg of 99% ee (74% based on the title compound).

D1 does not describe the preparation of the title compound but makes reference to *J. Med. Chem.* 1990, 33, 1645–1656 (D2). The yield of the title compound according to D2, starting from racemic 2-methylpiperazine was 35%.

M.Pt. 255.0–257.0° C.

$^1$H NMR (400 MHz, D$_2$O): δ 4.79 (D$_2$O, reference), 4.36 (2H, s), 3.73–3.64 (4H, m), 3.43 (1H, td J=13.7, 3.0 Hz), 3.34 (1H, td, J=12.7, 3.1 Hz), 3.17 (1H, dd, J=14.2 12.8 Hz), 1.41 (3H, d, J=6.1 Hz), 0.00 (TMS, reference).

$^{13}$C NMR (100 MHz, D$_2$O): δ 178.46 (s), 73.91 (d), 49.02 (d), 49.00 (MeOH, reference), 45.82 (t), 40.56 (t), 40.10 (t), 15.42 (q).

IR (diffuse reflectance) 3426 (s), 3011 (s), 2999 (s), 2888 (s), 2785 (s,b), 2740 (s,b), 2703 (s,b), 2649 (s,b), 2483 (s,b), 2483 (s,b), 2361 (s), 2354, 2340, 2248, 1638 (s), cm$_{-1}$.

HRMS (FAB) calcd for C$_5$H$_{12}$N$_2$+H$_1$ 101.1079, found 101.1080.

[α]$^{25}_D$=24° (c 1.00, water).

Anal. Calcd for C$_4$H$_6$O$_6$·C$_5$H$_{12}$N$_2$: C, 43.20; H, 7.25; N, 11.19. Found: C, 41.25; H, 745; N, 10.71.

Example 5

Preparation of (R)-2-methylpiperazine (R)-2-methylpiperazine, L-tartrate from Example 4 in H$_2$O (182 L), and Branched octanes (200 L) were added to a 4000 L reactor and stirred until dissolved. More branched octanes (530 L) were added to the 4000 L reactor followed by 50% NaOH (1120 kg) at a temperature between 35° C. and 52° C. The solution was heated to 80° C. and stirred for 2 h. The solution was settled and the lower aqueous phase was transferred to the 4000 L receiver. The solution in the 4000 L reactor was cooled to −21° C. and filtered onto a 48" Nutsche filter sending the filtrate to a 1200 L reactor. The 4000 L reactor and 48" Nutsche filter were rinsed with branched octanes (300 L). The solids were dried with 25° C. nitrogen and collected to yield 24.9 kg (67%) of the title compound of NLT 99% ee as determined by chiral HPLC assay. The aqueous solution in the 4000 L receiver was adjusted to pH 8.4 with acetic acid (812 kg) before disposal.

The yield of the title compound according to D2, starting from (R)-2-methyl-piperazine, L-tartrate was 42%.

M.Pt. 91–93° C.

$^1$H NMR (400 MHz, CDCl$_3$): δ 2.97–2.68 (6H, m), 2.35 (1H, dd, J=11.7, 10.2 Hz), 1.61 (2H, s), 1.00 (3H, d, J=6.7 Hz), 0.00 (TMS, reference).

$^{13}$C NMR (100 MHz, CDCl$_3$): δ 54.14 (t), 51.89 (d), 47.43 (t), 46.46 (t), 20.08 (q), 0.00 (TMS, reference). IR (mull) 3220 (s,b), 2819 (s), 2748 (s), 2042 (w), 1995 (w), 1981 (w), 1328, 1279, 1137, 1094, 960, 859 (s), 845 (s), 795 (s), 621 (s), cm$^{-1}$.

HRMS (FAB) calcd for C$_5$H$_{12}$N$_2$+H$_1$ 101.1079, found 101.1080.

[α]$^{25}_D$=−170 (c 0.85, CH$_2$Cl$_2$).

Anal. Calcd for C$_5$H$_{12}$N$_2$: C, 59.96; H, 12.07; N, 27.97. Found: C, 59.25; H, 11.71; N, 27.64.

Example 6

Preparation of (R)-3-methyl-1-tritylpiperazine

To the 1200 L reactor was dissolved (R)-2-methylpiperazine from Example 5 (25 kg) in CH$_3$CN (319 kg) at 15° C. to 25° C. until dissolution was complete (10 min.) After cooling to 5° C. to 10° C. Et$_3$N (63 kg) was added. To the 1200 L receiver trityl chloride (69.5 kg) was dissolved in CH$_2$Cl$_2$ (106 kg) at 15° C. to 25° C. The solution in the receiver was transferred to the reactor over 0.5 h with a CH$_2$Cl$_2$ rinse (27 kg), and the solution was heated to 20° C. to 30° C. The reaction was monitored by GLC and was complete in 1 h. The resulting slurry was cooled to 8° C. to 12° C., filtered onto a 48" Nutsche filter, and rinsed with CH$_3$CN (40 kg at 8° C. to 12° C.). The filter cake was dried using 50° C. to 55° C. nitrogen to afford 25.26 kg of the by-product Et$_3$NHCl (74% yield; easy to filter off the by-product). The filtrate was transferred to the 1200 L reactor and cooled further to −8° C. to −10° C. for 1 h. The resulting slurry was filtered onto a 24" Nutsche filter and rinsed with −8° C. to −10° C. CH$_3$CN (24 kg) sending the filtrate and rinse to the 1200 L receiver. The filter cake was dried with 50° C. to 55° C. nitrogen to afford another 2.98 kg Et$_3$NHCl (9% yield). The filtrate was transferred to the 1200 L reactor with a CH$_3$CN (10 kg) rinse, and distilled under vacuum to an oil of the title compound of 97.99% GC purity. The yield was quantitative.

M.Pt. 134–136° C.

$^1$H NMR (400 MHz, CDCl$_3$): δ 7.55–7.40 (6H, br s), 7.25 (6H, t, J=7.9 Hz), 7.14 (3H, t, J=7.1 Hz), 3.21–3.13 (2H, m), 3.10–2.90 (1H, br s), 2.94 (2H, t, J=13.0 Hz), 1.60 (1H, br s), 1.48 (1H, br s), 1.15 (1H, br s), 0.94 (3H, d, J=6.1 Hz), 0.00 (TMS, reference).

$^{13}$C NMR (100 MHz, CDCl$_3$): δ 129.41 (d), 127.46 (d), 125.96 (d), 125.83 (s), 56.12 (t), 51.23 (d), 48.73 (t), 46.45 (t), 20.05 (q), 0.00 (TMS, reference).

IR (diffuse reflectance) 2964, 2835, 2483 (w), 2350 (w), 2339 (w), 1956 (w), 1490, 1025, 909, 742 (s), 717, 710 (s), 703 (s), 697 (s), 629, cm$^{-1}$.

HRMS (EI) calcd for C$_{24}$H$_{26}$N$_2$ 342.2096, found 342.2101.

[α]$^{25}_D$=−12 (c 1.00, CH$_2$Cl$_2$).

Anal. Calcd for C$_{24}$H$_{26}$N$_2$: C, 84.17; H, 7.65; N, 8.18. Found: C, 84.12; H, 7.64; N, 7.94.

Example 7

Preparation of (2R)-1-(3-chloro-2-pyrazinyl)-2-methyl-4-tritylpiperazine

The product from Example 6 was dissolved in DMF (150 kg) at 25° C. The solution in the 1200 L reactor was cooled to 20° C. to 25° C. and transferred into the 1200 L receiver with a DMF rinse (30 kg). Anhydrous K$_2$CO$_3$ (103 kg) was added to the 1200 L reactor. The solution in the 1200 L receiver was transferred to the 1200 L reactor with a DMF rinse (30 kg). The 2,3-dichloropyrazine (48.5 kg) was added with a DMF rinse (4 L). The 1200 L reactor was heated to reflux at 127° C. to 133° C. Samples were taken every 12–18 h and monitored by GC. The reaction was complete in 41.5 h. The contents of the 1200 L reactor were cooled to 35° C. to 45° C. and transferred onto a 48" Nutsche filter sending the filtrate sent to the 1200 L receiver. MtBE rinses (2×200 kg at 35° C. to 45° C.) of the 1200 L reactor were transferred onto the 48" Nutsche filter sending the rinses to the 1200 L receiver. The filtrate in the 1200 L receiver was transferred to the 1200 L reactor with a MtBE rinse (50 kg). The solution in the 1200 L reactor was concentrated under vacuum to remove MtBE and DMF. MgSO$_4$ was added to a 48" Nutsche (181 kg) and the 1200 L receiver (45 kg). MtBE (625 kg) was added to the 1200 L reactor, heated to 40° C. to 45° C., and stirred to dissolve the title compound. The solution was cooled to 15° C. to 30° C. and transferred into the 1200 L receiver with a MtBE rinse (100 kg). The slurry in the 1200 L receiver was stirred for 3.5 h and filtered onto the 48" Nutsche filter sending the filtrate into the 1200 L reactor. The 1200 L receiver was rinsed with MtBE (2×250 kg at ~15° C. to 30° C.) and transferred to the 48" Nutsche filter sending the rinses into the 1200 L reactor. The filtrate in the 1200 L reactor was distilled under vacuum to afford the title compound of 87.83% GC purity. The yield was quantitative.

$^1$H NMR (400 MHz, d$_6$-DMSO at 87° C.): δ 8.18 (1H, d, J=2.5 Hz), 7.89 (1H, d, J=2.1 Hz), 7.47 (6H, d, J=7.6 Hz), 7.31 (6H, 5, J=7.6 Hz), 7.18 (3H, t, J=7.4 Hz), 4.31–4.26 (1H, m), 3.66 (1H, ddd, J=12.4, 9.9, 2.5 Hz), 3.48 (1H, br d,J=12.7 Hz), 2.72 (1H, br d, J=11.2 Hz), 2.59 (1H, br d, J=10.7 Hz), 2.49 (d$_6$-DMSO, reference), 2.14 (1H, br dd, J=11.2, 2.0 Hz), 1.89 (1H, br t, J=9.9 Hz), 1.37 (3H, d, J=6.6 Hz).

$^{13}$C NMR (100 MHz, d$_6$-DMSO at 87° C.): δ 153.85 (s), 141.51 (s), 139.79 (d), 134.86 (d), 128.57 (d), 127.02 (d), 135.60 (d), 76.07 (s), 52.09 (t), 50.84 (d), 47.68 (t), 44.40 (t), 39.52 (d$_6$-DMSO, reference), 15.39 (q).

IR (diffuse reflectance) 2963 (s), 2350 (w), 2317 (w), 1959 (w), 1921 (w), 1906 (w), 1501, 1488, 1465, 1443 (s), 1411 (s), 1143 (s), 1022, 744, 708 (s), cm$^{-1}$.

HRMS (FAB) calcd for C$_{28}$H$_{27}$ClN$_4$+H$_1$ 455.2002, found 455.2004.

$[\alpha]^{25}_D$=−36° (c 0.98, CH$_2$Cl$_2$).

Anal. Calcd for C$_{28}$H$_{27}$ClN$_4$: C, 73.91; H, 5.98; N, 12.31; Cl, 7.79. Found: C, 74.26; H, 6.84; N, 10.74.

Example 8

Preparation of (2R)-1-(3-chloro-2-pyrazinyl)-2-methylpiperazine

To the 1200 L reactor containing the product from Example 7 was added IPA (707 kg). Stirring at reflux (77° C. to 83° C.) was continued until dissolution was complete. The solution in the 1200 L reactor was transferred to the 4000 L reactor with a IPA rinse (100 kg) and heated to reflux (77° C. to 83° C.). A 10% sulfuric acid solution (giving a clean reaction) was prepared in the 4000 L receiver by adding water (245 L) and 98% H$_2$SO$_4$ (27 kg). The H$_2$SO$_4$ solution was stirred for 10 minutes at 20° C. to 60° C. and transferred to the 4000 L reactor while maintaining the 4000 L reactor temperature between 60° C. to 85° C. The 4000 L receiver was rinsed with water (25 L) sending the rinse to the 4000 L reactor. The 4000 L reactor was heated to reflux (77° C. to 83° C.). The reaction was monitored by GC and was complete in 30 min. The contents in the 4000 L reactor were cooled to 35° C. to 40° C. The IPA was removed under vacuum distillation. Water (1265 L) and MtBE (511 kg) was added to the 4000 L reactor. After stirring and settling, the aqueous layer was transferred into the 4000 L receiver. The MtBE layer in the 4000 L reactor was disposed. MtBE (511 kg) was added to the 4000 L receiver, the solution was stirred and settled for at least 15 min. The aqueous layer was transferred to the 4000 L reactor. The MtBE layer in the 4000 L receiver was disposed. The pH was adjusted to 9.5 to 10.5 using 47% K$_2$CO$_3$ (206 kg) with a water rinse (50 L) of the add line. CH$_2$Cl$_2$ (2×765 L, 1×255 L) was used to extract the title compound from the 4000 L reactor sending the CH$_2$Cl$_2$ extractions into the 4000 L receiver. The organic solution in the 4000 L receiver was transferred to the 4000 L reactor with a CH$_2$Cl$_2$ rinse (100 L). The CH$_2$Cl$_2$ was removed by distillation. Toluene (1000 L) was added to the 4000 L reactor and subsequently removed by vacuum distillation to afford a toluene solution of the title compound of 95.77% GC purity. The yield was quantitative.

Summarizing the steps of Examples 5–8, the yield of the product from Example 8 was 67% starting from (R)-2-methylpiperazine, L-tartrate. According to D1, the yield of the same product was 60% starting from (R)-2-methylpiperazine, L-tartrate. The step described in D1 corresponding to the process in Example 8 was performed in a mixture of hot ethanol and 10% aqueous hydrochloric acid.

$^1$H NMR (400 MHz, CDCl$_3$): δ 8.12 (1H, d, J=2.6 Hz), 7.87 (1H, d, J=2.6 Hz), 4.18–4.12 (1H, m), 3.39 (2H, t, J=3.6 Hz), 3.12 (1H, dd, J=12.2, 3.6 Hz), 3.06 (1H, dt, J=12.2, 3.6 Hz), 3.02–2.95 (1H, m), 2.81 (1H, dd, J=12.2, 4.0 Hz), 1.90 (1H, br s), 1.21 (3H, d, J=6.6 Hz), 0.00 (TMS, reference).

$^{13}$C NMR (100 MHz, CDCl$_3$): δ 155.15 (s), 140.85 (s), 139.93 (d), 135.15 (d), 51.06 (d), 50.98 (t), 45.94 (t), 45.10 (t), 14.72 (q), 0.00 (TMS, reference).

IR (liq.) 2940, 2389 (w), 2149 (w), 1996 (w), 1556 (s), 1504 (s), 1459 (s), 1440 (s), 1415 (s), 1367, 1330 (s), 1132 (s), 1107 (s), 1100 (s), 1049 (s), cm$^{-1}$.

$[\alpha]^{25}_D$=−430 (c 0.59, CH$_2$Cl$_2$).

HRMS (FAB) calcd for C$_9$H$_{13}$ClN$_4$+H$_1$ 213.0907, found 213.0909.

Anal. Calcd for C$_9$H$_{13}$ClN$_4$: C, 50.83; H, 6.16; N, 26.34. Found: C, 50.48; H, 6.19; N, 26.47.

Example 9

Preparation of (2R)-1-(3-chloro-2-pyrazinyl)-2-methylpiperazine, Hydrochloride

To a 200 L reactor was added the product from Example 8 in toluene solution (ca 25 kg thereof in 93 kg solution) with an EtOAc rinse (10 kg). Solvent was removed using vacuum until a volume of 35 L was reached. To remove most of the toluene, EtOAc (2×90 kg) was added to the 200 L reactor and distilled until a volume of 35 L was reached. EtOAc (90 kg) was added to the 200 L reactor and heated to reflux (78° C.). The slurry in the 200 L reactor was cooled to 55° C. to 60° C., filtered through a bag filter to remove solid impurities sending the filtrate to the 200 L receiver. The 200 L reactor was rinsed with EtOAc (5 kg) sending the rinse into the 200 L receiver. The solution in the 200 L receiver was transferred to the 400 L reactor with an EtOAc rinse (5 kg). 37% HCl (9.0 kg) was added to the 200 L receiver and rinsed with EtOAc (9 kg). The 37% HCl solution was transferred to the 200 L reactor while maintaining a temperature of 73° C. to 80° C. in the 200 L reactor. The solution in the 200 L reactor was maintained at 72° C. for 10 min. The solution was cooled to −25° C. to −30° C. for 2 h 45 min. The resulting slurry in the 200 L reactor was filtered onto an 18" Nutsche filter sending the filtrate into the 200 L receiver. The reactor and nutsche were rinsed with −25° C. EtOAc (3×45 kg) sending the filtrate into drums. The filter cake was dried to afford 24.5 kg (79%) of the title compound of 98.4% GC purity. A 2$^{nd}$ similar run gave 23.1 kg for a total of 47.6 kg (77%).

M.Pt. 209.0–210.5° C.

$^1$H NMR (400 MHz, d$_4$-MeOH): δ 8.29 (1H, d, J=2.6 Hz), 8.07 (1H, d, J=2.6 Hz), 4.83 (2H, br s), 4.30 (1H, sextet, J=5.8 Hz), 3.68–3.56 (2H, m), 3.40 (1H, dd, J=14.2, 4.7 Hz), 3.37 (1H, m), 3.31 (1H, br s), 3.23 (1H, dd, J=12.7, 5.1 Hz), 1.30 (3H, d, J=6.6 Hz), 0.00 (TMS, reference).

$^{13}$C NMR (100 MHz, d$_4$-MeOH): δ 155.45 (s), 143.28 (s), 141.90 (d), 138.91 (d), 50.32 (d), 48.60 (t), 44.26 (t), 43.41 (t), 15.41 (q), 0.00 (TMS, reference).

IR (diffuse reflectance) 2934, 2802, 2781 (s), 2744 (s), 2717, 2684, 2470, 2425, 2351 (w), 2335 (w), 2269 (w), 1453 (s), 1412 (s), 1148 (s), 881 cm$^{-1}$.

HRMS (FAB) calcd for C$_9$H$_{13}$ClN$_4$+H$_1$ 213.0907, found 213.0912.

[α]$^{25}$$_{D=-24}$° (c 0.92, water).

Anal. Calcd for $C_9H_{13}ClN_4 \cdot HCl$: C, 43.39; H, 5.66; N, 22.49. Found: C, 43.48; H, 5.75; N, 22.37.

Example 10

Preparation of (2R)-methyl-1-{3-[2-(3-pyridinyloxy)ethoxy]-2-pyrazinyl}piperazine, Fumarate To a 400 L reactor was added a solution of the product from Example 2A in MeOH (ca. 12.4 kg in 90 L solution) followed by a MeOH rinse (5 kg). The solution was distilled to a volume of 50 L. The fumaric acid (4.6 kg) was added to the 400 L reactor using an addition funnel. The slurry was stirred for 45 min at 25° C. to 30° C. until all the solids dissolved. MtBE (133 kg) was slowly added, the resulting slurry was cooled to 30° C., and the solids were filtered onto an 18" Nutsche sending the filtrate into the 400 L receiver. The 400 L reactor and 18" Nutsche were rinsed with MtBE (16 kg) sending the rinse into the 400 L receiver. The title compound was dried and packaged to yield 12.3 kg (58%) of 97.4% GC purity. The product purity can be slightly improved by repeating the crystallization.

M.Pt. 125.5–126.5° C.

$^1$H NMR (400 MHz, $d_4$-MeOH): δ 8.27 (1H, d, J=3.1 Hz), 8.15 (1H, d, J=4.5 Hz), 7.78 (1H, d, J=2.6 Hz), 7.65 (1H, d, J=23.1 Hz), 7.48 (1H, dd, J=8.1, 2.5 Hz), 7.38 (1H, dd, J=8.5, 4.9 Hz), 6.69 (2H, s), 4.36 (4H, br s), 4.74 (2H, q, J=4.6 Hz), 4.69–4.63 (1H, m), 4.48 (1H, t, J=4.3 Hz), 3.99 (1H, dt, J=11.7, 3.1 Hz), 3.51 (1H, ddd, J=14.7, 11.2, 3.0 Hz), 3.30–3.26 (2H, m), 3.22–3.15 (2H, m), 1.28 (3H, d, J=6.7 Hz), 0.00 (TMS, reference).

$^{13}$C NMR (100 MHz, $d_4$-MeOH): δ 171.20 (s), 156.98 (s), 152.27 (s), 147.16 (s), 142.67 (d), 138.51 (d), 136.14 (d), 135.11 (d), 133.33 (d), 125.94 (d), 123.39 (d), 67.97 (t), 65.75 (t), 48.16 (t), 48.54 (d), 44.17 (t), 40.07 (t), 14.79 (q), 0.00 (TMS, reference).

IR (diffuse reflectance) 3047 (s), 3028 (s,b), 2985 (s,b), 2976 (s), 2962 (s), 2350 (w), 2339 (w), 2318 (w), 2063 (w), 1990 (w), 1710 (s), 1442 (s), 1261 (s), 1206 (s), 1190 (s), cm$^{-1}$.

[α]$^{25}$$_D$=−20° (c 0.98, water).

Anal. Calcd for $C_{16}H_{21}N_5O_2 \cdot C_4H_4O_4$: C, 55.68; H, 5.84; N, 16.23. Found: C, 55.01; H, 5.88; N, 15.65.

Example 11

Comparison of the Properties of Different Salts of Example 2A

The following salts were prepared by Chemical development, Stockholm and Kalamazoo and evaluated by Pharmaceutical Development, Nerviano:

(2R)-methyl-1-{3-[2-(3-pyridinyloxy)ethoxy]-2-pyrazinyl}piperazine (free base; see Example 2A)

(2R)-methyl-1-{3-[2-(3-pyridinyloxy)ethoxy]-2-pyrazinyl}piperazine, L-malate (see Example 3A)

(2R)-methyl-1-{3-[2-(3-pyridinyloxy)ethoxy]-2-pyrazinyl}piperazine, fumarate (see Example 10)

(2R)-methyl-1-{3-[2-(3-pyridinyloxy)ethoxy]-2-pyrazinyl}piperazine, hydrochloride (see D1, Example 173)

(2R)-methyl-1-{3-[2-(3-pyridinyloxy)ethoxy]-2-pyrazinyl}piperazine, acetate (2R)-methyl-1-{3-[2-(3-pyridinyloxy)ethoxy]-2-pyrazinyl}piperazine, benzoate (2R)-methyl-1-{3-[2-(3-pyridinyloxy)ethoxy]-2-pyrazinyl}piperazine, cinnamate.

Identification (NMR and Elementary Analysis)

Positive data for most salts, except for the free-base and the hydrochloride. NMR analysis was positive for the free-base. The hydrochloride showed problems related to the stoichiometric ratio.

Crystallinity (X-rays)

Positive results for free base, acetate, benzoate, L-malate, and cinnamate were obtained. Most samples were substantially crystalline. Hydrochloride and especially fumarate came out to be of lower crystallinity.

Hygroscopicity (DVS, Storage at RT/Different RHs and at 40° C./75% RH)

Positive results were obtained on benzoate, L-malate, and cinnamate. They showed lower hygroscopicity (<5% equilibrium moisture contents at RT/90% RH). Moisture-related effects on the bulk solid state properties of the benzoate salt were observed (cake formation and darkening) but without changes on the DSC pattern. Acetate and hydrochloride were deliquescent (the former at RT/75% RH while the latter at higher values). Fumarate was subjected to hydrate conversion upon exposition at RT/90% RH. Exposition to 40° C./75% RH showed good behavior of cinnamate and L-malate, recovered as powders showing substantially unchanged properties.

Solubility (Water, pH 1.2 and pH 7.4 buffers)

Positive results were obtained for all salts (≅300 mg/ml FBE) with the exception of cinnamate whose solubility in water is about 8–10 mg/ml FBE.

Intrinsic Dissolution Rate (pH 1.2)

All results confirmed the solubility data. IDRs were about $10^{-1}$ mgsec$^{-1}$ cm$^{-2}$ while cinnamate had much lower dissolution rate ($10^{-3}$ that means −2 order of magnitude lower than the others). Acetate salt showed problem during tablet preparation (sticking to the punch).

Chemical Stability (2 weeks at 65° C.)

Positive data for benzoate, L-malate, and cinnamate were obtained. Fumarate and acetate seemed to be the less stable salts either at RT/90% RH and at high temperature. Formation of the reaction product with fumaric acid was also observed. These samples showed unchanged DSC patterns except for the acetate (peak broadening).

Polymorphism

The tested conditions (RT evaporation, cooling crystallization at −20° C. in different solvent or mixtures) did not show other polymorphs of benzoate and L-malate salts.

Manufacturing Method

Benzoate, L-malate, and cinnamate seemed to be easier to crystallize than fumarate, hydrochloride and free base.

Toxicological Acceptability

There are few marketed drugs that are cinnamate salts and no much information in literature. Oral LD$_{50s}$ in rats are about 2500 mg/kg and 5 g/kg in mice.

Malic acid is an intermediate in the citric acid cycle and occurs naturally in apple and many fruits. It is FDA approved as food additive. A lot of drugs are approved in Europe and US as malate salts.

In summary, of the salts examined above, (2R)-methyl-1-{3-[2-(3-pyridinyloxy)ethoxy]-2-pyrazinyl}piperazine, L-malate seems to be the best choice of the salts examined due to its high crystallinity, low hygroscopicity, high chemical stability and low toxicity.

Example 12

Comparison of the Properties of Different Salts of Example 2B

The following salts have been prepared:
(2R)-1-(3-{2-[(2-ethoxy-3-pyridinyl)oxy]ethoxy}-2-pyrazinyl)-2-methylpiperazine (free base, see Example 2B)
(2R)-1-(3-{2-[(2-ethoxy-3-pyridinyl)oxy]ethoxy}-2-pyrazinyl)-2-methylpiperazine, acetate
(2R)-1-(3-{2-[(2-ethoxy-3-pyridinyl)oxy]ethoxy}-2-pyrazinyl)-2-methylpiperazine, fumarate (see D1, Example 200)
(2R)-1-(3-{2-[(2-ethoxy-3-pyridinyl)oxy]ethoxy}-2-pyrazinyl)-2-methylpiperazine, succinate (see Example 3B).

Crystallinity (Powder X-ray Diffraction)

For the succinate salt, the degree of crystallinity was very high. The degree of crystallinity decreased in the order succinate>acetate>fumarate.

Thermal Properties

For the free base and the acetate salt the melting temperature onset was low (81° C. and 96° C., respectively). These low melting points can be drawbacks in future development work. For the succinate and fumarate salts the thermal properties were fair since the extrapolated melting temperature onset was 123° C. and 149° C., respectively.

Hygroscopicity

All but the acetate salt had acceptable properties with repect to hygroscopicity. The acetate salt was very hygroscopic and showed a pronounced hysteresis at high values of relative humidity.

Solubility and Intrinsic Dissolution Rate

The solubility of the succinate salt, in all investigate media, was at least 250 mg/ml.

For the fumarate salt the solubility was >93 mg/ml in 0.9% w/w NaCl and >68 mg/ml in phosphate buffer at pH 7.4. Hence, the solubility of succinate was in all instances higher than the fumarate salt.

The intrinsic dissolution rate studies indicated the dissolution rate to increase according to the order base<fumarate<succinate.

In conclusion, with the respect to the solubility and the intrinsic dissolution rate, the succinate salt proved to have the most favourable qualities of the salts and the free base studied.

Impurities

Analysis (LC-UV-MS) of the fumarate salt revealed the presence of a fumarate adduct (~1%) and the formation of dimers of the free base (0.2%). The fumarate adduct may be a Michael adduct between the piperazine ring and fumaric acid.

Conclusion

The succinate salt hade the overall best state properties, good crystallinity, a relatively high melting point, a high solubility and a high intrinsic dissolution rate. The acetate salt proved to be both hygroscopic and to have a low melting range. The solubility, intrinsic dissolution rate and the degree of crystallinity of the fumarate salt was inferior to that of the succinate salt. In view of the properties of the different salts investigated the best candidate for further development is the succinate salt.

Example 13

Comparison of the Properties of Different Salts of Example 2C

The following salts have been prepared:
(2R)-1-[3-(2-{[2-(2-dimethylaminoethoxy)-3-pyridinyl]oxy}ethoxy)-2-pyrazinyl]-2-methylpiperazine (free base; see Example 2C)
(2R)-1-[3-(2-{[2-(2-dimethylaminoethoxy)-3-pyridinyl]oxy}ethoxy)-2-pyrazinyl]-2-methylpiperazine, phosphoric acid salt (see Example 3C)
(2R)— 1-[3-(2-{[2-(2-dimethylaminoethoxy)-3-pyridinyl]oxy}ethoxy)-2-pyrazinyl]-2-methylpiperazine, acetate
(2R)-1-[3-(2-{[2-(2-dimethylaminoethoxy)-3-pyridinyl]oxy}ethoxy)-2-pyrazinyl]-2-methylpiperazine, citrate
(2R)-1-[3-(2-{[2-(2-dimethylaminoethoxy)-3-pyridinyl]oxy}ethoxy)-2-pyrazinyl]-2-methylpiperazine, edeteate
(2R)-1-[3-(2-{[2-(2-dimethylaminoethoxy)-3-pyridinyl]oxy}ethoxy)-2-pyrazinyl]-2-methylpiperazine, oxalate
(2R)-1-[3-(2-{[2-(2-dimethylaminoethoxy)-3-pyridinyl]oxy}ethoxy)-2-pyrazinyl]-2-methylpiperazine, succinate
(2R)-1-[3-(2-{[2-(2-dimethylaminoethoxy)-3-pyridinyl]oxy}ethoxy)-2-pyrazinyl]-2-methylpiperazine, D-tartrate
(2R)-1-[3-(2-{[2-(2-dimethylaminoethoxy)-3-pyridinyl]oxy}ethoxy)-2-pyrazinyl]-2-methylpiperazine, 1,3,5-benzenetricarboxylate
(2R)-1-[3-(2-{[2-(2-dimethylaminoethoxy)-3-pyridinyl]oxy}ethoxy)-2-pyrazinyl]-2-methylpiperazine, galactareate (mucic acid salt)
(2R)-1-[3-(2-{[2-(2-dimethylaminoethoxy)-3-pyridinyl]oxy}ethoxy)-2-pyrazinyl]-2-methylpiperazine, 1,5-naphthalenedisulfonate
(2R)-1-[3-(2-{[2-(2-dimethylaminoethoxy)-3-pyridinyl]oxy}ethoxy)-2-pyrazinyl]-2-methylpiperazine, terephthalate.

Crystallinity (Powder X-ray Diffraction)

The acetate- and the oxalate salt had a high degree of crystallinity whilst the crystallinity of the succinate salt and the phosphoric acid salt ranged from predominantely crystalline to moderately crystallinity. The D-tartrate salt had a low degree of crystallinity. Two salts, edeteate and citrate proved to be practically amorphous. The free base is a viscous oil at ambient conditions. The benzenetricarboxylate, naphthalenedisulfonate and terephtalate were predominantly crystalline, whilst the galactareate was partially amorphous.

Hygroscopicity

The acetate, citrate, edeteate, succinate and D-tartrate salts proved to be very hygroscopic and deliquescent. Also the free base was hygroscopic. The hygroscopicity of the the oxalate and phosphoric acid salt was low. The hygroscopicity of the benzenetricarboxylate, naphthalenedisulfonate and terephthalate was low, moderate and hight (deliquescent), respectively.

Solubility

The solubility of the phosphoric acid salt was, in all investigated media, not less than 590 mg/ml. Preliminary studies indicated the benzenetricarboxylic acid to have a solubility of >19 mg/ml in SGF (simulated gastric fluid without enzymes; pH of filtrate 2.9), 11 mg/ml in SIF (simulated intestinal fluid without enzymes; pH of filtrate 4.2) and in purified water 4 mg/ml (pH of filtrate 3.6). The solubility of the naphthalenedisulfonate was high >540 mg/ml. Preliminary studies of the solubility of the terephthalate salt in purified water indicated the solubility to be low (<1 mg/ml).

Toxicological Acceptability

Regarding the oxalate salt although its solid state properties are good it was deemed inappropriate due to toxicological reasons. The benzenetricarboxylate salt had the overall most promising solid state properties but the solubility was lower than for the phosphoric acid salt and requires a toxicological evaluation. The phosphoric acid salt was deemed to be the best choice of the salts regarding high crystallinity, low hygroscopicity, high solubility, and low toxicity.

The invention claimed is:

1. A process for the preparation of a pharmaceutically acceptable salt of a compound of the general formula (I):

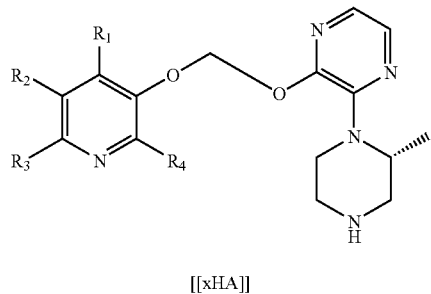

(I)

comprising the steps of:

(i) O-alkylating a 3-pyridinol derivative of the general formula (II) or the corresponding hydrochloride:

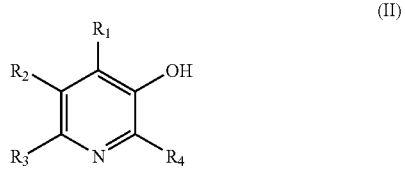

(II)

to give another 3-pyridinol derivative of the general formula (III):

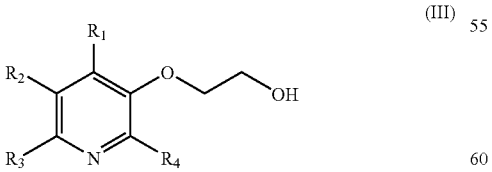

(III)

(ii) reacting the 3-pyridinol derivative of the general formula (III) with (2R)-1-(3-chloro-2-pyrazinyl)-2-methylpiperazine of the formula (IV) in the presence of an alkali metal tert-butoxide or an alkali earth metal tert-butoxide,

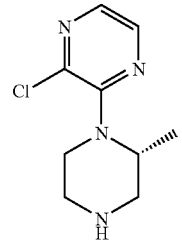

(IV)

to give a compound of the general formula (I):

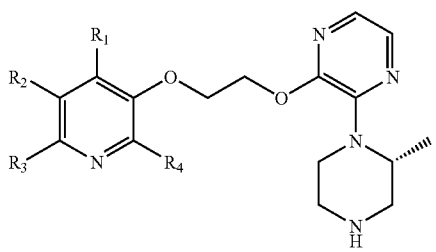

(V)

(iii) converting the compound of the general formula (I) to a pharmaceutically acceptable salt thereof by treatment with a pharmaceutically acceptable organic or inorganic acid, wherein each of $R_1$, $R_2$, $R_3$, and $R_4$, independently, is hydrogen, halogen, $C_1$–$C_6$-alkyl, $C_1$–$C_6$-alkoxy, and di-$C_1$–$C_6$-alkylamino-$C_2$–$C_6$-alkoxy.

2. The process according to claim 1, wherein (2R)-1-(3-chloro-2-pyrazinyl)-2-methylpiperazine of the formula (IV) is prepared by:

(iv) acidification of racemic 2-methylpiperazine of the formula (VI):

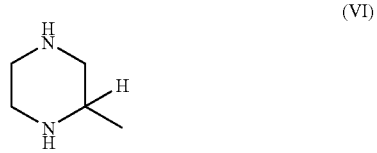

(VI)

with L-tartaric acid and fractional crystallization to give (R)-2-methylpiperazine, L-tartrate of the formula (VII):

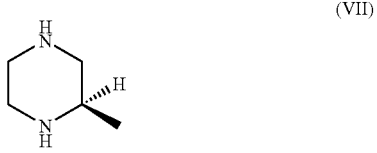

(VII)

x L-tartrate (v) basification of (2R)-2-methylpiperazine, L-tartrate of the formula (VII) to give (R)-2-methylpiperazine of the formula (VIII):

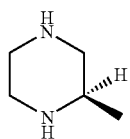
(VIII)

(vi) tritylation of (R)-2-methylpiperazine of the formula (VIII) to give (R)-3-methyl-1-tritylpiperazine of the formula (IX):

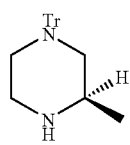
(IX)

(vii) condensation of (R)-3-methyl-1-tritylpiperazine of the formula (IX) with 2,3-dichloropyrazine to give (2R)-1-(3-chloro-2-pyrazinyl)-2-methyl-4-tritylpiperazine of the formula (X):

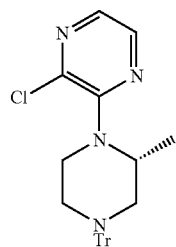
(X)

(viii) detritylation of (2R)-1-(3-chloro-2-pyrazinyl)-2-methyl-4-tritylpiperazine of the formula (X) to give (2R)-1-(3-chloro-2-pyrazinyl)-2-methylpiperazine of the formula (IV), (ix) and conversion of (2R)-1-(3-chloro-2-pyrazinyl)-2-methylpiperazine of the formula (IV) to a suitable acid addition salt.

3. The process according to claim 1, wherein the alkali metal tert-butoxide is potassium tert-butoxide.

4. The process according to any one of claims 1 to 3, wherein step (ii) is performed in a solvent system comprising tetrahydrofuran.

5. The process according to claim 2, wherein step (iv) is performed by using water and ethanol as solvents.

6. The process according to claim 2, wherein step (v) is performed by using a hydroxide as a base.

7. The process according to claim 2, wherein step (vi) is performed with trityl chloride in the presence of triethylamine.

8. The process according to claim 2, wherein step (vii) is performed in the presence of an alkali metal carbonate or an alkali earth metal carbonate, with dimethyl formamide as a solvent.

9. The process according to claim 2, wherein step (viii) is performed in 10% sulfuric acid in isopropanol.

10. The process of claim 2, wherein the salt formed in step (ix) is a hydrochloride salt.

11. The process of claim 1, wherein (2R)-1-(3-chloro-2-pyrazinyl)-2-methylpiperazine of the formula (IV) is in the form of an acid addition salt.

* * * * *